United States Patent
Benjahad

(10) Patent No.: US 8,080,669 B2
(45) Date of Patent: Dec. 20, 2011

(54) PROCESS FOR THE SYNTHESIS OF 2-AMINOXAZOLE COMPOUNDS

(75) Inventor: Abdellah Benjahad, Champigny sur Marne (FR)

(73) Assignee: AB Science, Paris (FR)

( * ) Notice: Subject to any disclaimer, the term of this patent is extended or adjusted under 35 U.S.C. 154(b) by 384 days.

(21) Appl. No.: 12/299,901

(22) PCT Filed: May 11, 2007

(86) PCT No.: PCT/EP2007/054564
§ 371 (c)(1),
(2), (4) Date: Feb. 10, 2009

(87) PCT Pub. No.: WO2007/131953
PCT Pub. Date: Nov. 22, 2007

(65) Prior Publication Data
US 2009/0192317 A1    Jul. 30, 2009

Related U.S. Application Data

(60) Provisional application No. 60/799,674, filed on May 12, 2006.

(51) Int. Cl.
*C07D 263/48*    (2006.01)

(52) U.S. Cl. ...................................................... 548/233

(58) Field of Classification Search ........................ None
See application file for complete search history.

(56) References Cited

U.S. PATENT DOCUMENTS

2005/0228031 A1    10/2005    Bilodeau et al.

OTHER PUBLICATIONS

Nodiff, E., et al.; "Synthesis of phenothiazines. III. Derivatives of hydroxyl-and mercaptophenothiazines"; Journal of Organic Chemistry, vol. 25, No. 1, Jan. 1, 1960, pp. 60-65, XP002444426.

Nodiff, E. A., et al.; "Synthesis of phenothiazine. III. Derivatives of hydroxyl-and mercaptophenothiazines" Journal of Organic Chemistry, vol. 25, No. 1, Jan. 1960, pp. 60-65.

*Primary Examiner* — Kamal Saeed
(74) *Attorney, Agent, or Firm* — Foley & Lardner LLP

(57) ABSTRACT

The present invention relates to a process for synthesizing in good yield substituted 2-aminoaryloxazole compounds of formula I which are useful as certain tyrosine kinase inhibitors and more particularly as c-kit, bcr-abl, Flt-3 and mutant forms thereof.

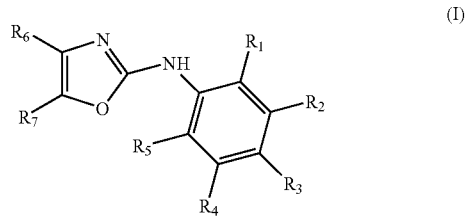

9 Claims, No Drawings

PROCESS FOR THE SYNTHESIS OF 2-AMINOXAZOLE COMPOUNDS

The present invention relates to a process for synthesizing compounds having the formula (I) which are useful as certain tyrosine kinase inhibitors and more particularly as c-kit, bcr-abl, Flt-3 and mutant forms thereof. More specifically, it relates to the synthesis in good yield of substituted 2-aminoaryloxazole compounds of formula I wherein groups R1-R7, identical or different, are as described hereinafter.

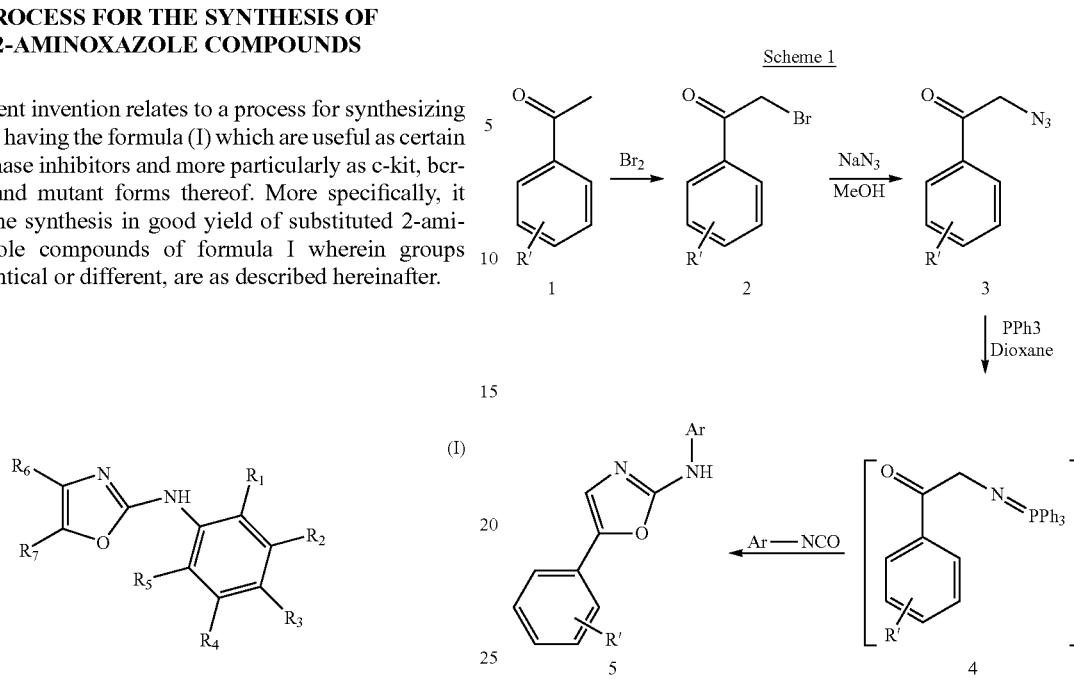

BACKGROUND OF THE INVENTION

We have recently found that compounds corresponding to substituted oxazole derivatives (WO2005040139) are potent and selective of certain tyrosine kinase inhibitors and more particularly of c-kit, bcr-abl, Flt-3 and mutant forms thereof. These compounds are good candidates for treating diseases such as autoimmunes diseases, inflammatory diseases, cancers and mastocytosis. In view of the growing interest of such compounds as candidate medicament, a process allowing high scale production is needed.

Several publications have described the synthesis of functionalized 2-aminoaryloxazole compounds. Examples include, Turchi, I. J. (Ed. Heterocyclic Compounds, J. Wiley and sons: N.Y., 1986); U.S. Patent US 2002/0143176A1 as well as publications by Froyen P. (Phosphorus, Sulfur and Silicon, 1991, vol 60 pp. 81-84) and Murali Dhar, T. G., et al. (Bioorganic § Medicinal Chemistry Letters, 2002, vol 12, pp. 3125-3128). However, and as summarized below, conventional methodologies have synthetic disadvantages concerning one or more of these characteristics: yield, scalability to multi-gram synthesis, highly reactive by-product formation, hazardous reaction conditions, impurity formation, number of synthetic steps, reaction conditions, and purifications. For example, the synthesis of 2-aminoaryloxazole 5 via Iminophosphorane 4 (Scheme 1) present two major disadvantages: a risk of explosions due to the presence of azide 3 (Murali Dhar, T. G., et al. (Organic Letters, 2002, vol 4 (12), pp. 2091-2093)), and rapid decomposition under reaction conditions of 2-Azido Ketone 3, when 5-aromatic moiety is highly functionalized. This decomposition adversely affects product recovery, and the reaction is characterized by numbers of byproducts and a yield that is too low to allow for its implementation in a scale-up process.

In contrast with conventional methodologies, the present invention provides a synthetic method that is characterized by at least one of the following features: good yields, with embodiments producing at least about 70% yield of the functionalized 2-aminooxazole derivative of interest; regioselectivity; purification by simple procedures, such as crystallization; and suitability for the production of multi-gram quantities of the products of interest. A series of 2-aminooxazole derivatives are described herein. Also described are methods for preparing these derivatives, that are amenable to large-scale procedures.

The process according to the present invention presents the advantages of obtaining 5-functionalised oxazole in good yield such 5-carboxyl-oxazole or 5-cyano-oxazole.

DESCRIPTION

The present invention relates to a process for the preparation of compounds of formula (I), comprising a condensation of compound of formula (II) and an acetamide derivative of formula (III), in very mild conditions which are in a solvent comprising a base:

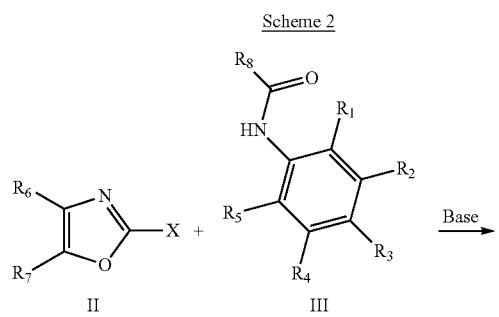

[Chemical structure diagram of formula I: an oxazole ring bearing R6, R7, R8 substituents connected via NH to a phenyl ring bearing R1, R2, R3, R4, R5]

I

Wherein substituents R1-R8 and X in are defined as follows:

R1, R2, R3, R4 and R5 each independently are selected from hydrogen, halogen (selected from F, Cl, Br or I), a linear or branched alkyl group containing from 1 to 10 carbon atoms and optionally substituted with one or more heteroatoms such as halogen (selected from F, Cl, Br or I), oxygen, and nitrogen, the latter optionally in the form of a pendant basic nitrogen functionality; as well as trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, SO2-R, and SO2NH—R wherein R is a linear or branched alkyl group containing from 1 to 10 carbon atoms and optionally substituted with at least one heteroatom, notably a halogen (selected from F, Cl, Br or I), oxygen, and nitrogen, the latter optionally in the form of a pendant basic nitrogen functionality.

R6 and R7 each independently are selected from:
i) hydrogen, a halogen (selected from F, Cl, Br or I), or
ii) an alkyl[1] group defined as a linear, branched or cycloalkyl group containing from 1 to 10 carbon atoms and optionally substituted with one or more heteroatoms such as halogen (selected from F, Cl, Br or I), oxygen, and nitrogen (the latter optionally in the form of a pendant basic nitrogen functionality); as well as trifluoromethyl, carboxyl, cyano, nitro, formyl; as well as CO—R, COO—R, SO2-R, and SO2NH—R wherein R is a linear or branched alkyl group containing 1 to 10 carbon atoms and optionally substituted with at least one heteroatom, notably a halogen (selected from F, Cl, Br or I), oxygen, and nitrogen, the latter optionally in the form of a pendant basic nitrogen functionality; as well as a cycloalkyl or aryl[1] or heteroaryl[1] group optionally substituted by a pendant basic nitrogen functionality, or
(iii) an aryl[1] group defined as phenyl or a substituted variant thereof bearing any combination, at any one ring position, of one or more substituents such as
  halogen (selected from I, F, Cl or Br);
  an alkyl[1] group;
  a cycloalkyl or aryl or group optionally substituted by a pendant basic nitrogen functionality;
  trifluoromethyl, O-alkyl[1], carboxyl, cyano, nitro, formyl, hydroxy, NH-alkyl[1], N(alkyl[1])(alkyl[1]), and amino, the latter nitrogen substituents optionally in the form of a basic nitrogen functionality;
  NHSO2-R or NHSO2NH—R or CO—R or COO—R or SO2-R or SO2NH—R wherein R corresponds to hydrogen, alkyl[1], aryl, or
(iv) a heteroaryl[1] group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents such as
  halogen (selected from F, Cl, Br or I);
  an alkyl[1] group;
  a cycloalkyl or aryl group optionally substituted by a pendant basic nitrogen functionality,
  trifluoromethyl, O-alkyl[1], carboxyl, cyano, nitro, formyl, hydroxy, NH-alkyl[1], N(alkyl[1])(alkyl[1]), and amino, the latter nitrogen substituents optionally in the form of a basic nitrogen functionality;
  NHSO2-R or NHSO2NH—R or CO—R or COO—R or SO2-R or SO2NH—R wherein R corresponds to hydrogen, alkyl[1], or
(v) an O-aryl[1], or NH-aryl[1], or O-heteroaryl[1] or NH-heteroaryl[1] group
(vi) trifluoromethyl, O-alkyl[1], carboxyl, cyano, nitro, formyl, hydroxy, NH-alkyl[1], N(alkyl[1])(alkyl), and amino, the latter nitrogen substituents optionally in the form of a basic nitrogen functionality, or
(vi) NHSO2-R or NHSO2NH—R or CO—R or COO—R or SO2-R or SO2NH—R wherein R corresponds to hydrogen, alkyl[1] or aryl.

R8 is an alkyl, a cycloalkyl, an aryl or alkyloxy groups, said groups are substituted or not with a halogen atom as F, Cl, Br or I.

Substituent X is:
i) halogen (selected from F, Cl, Br or I) or
ii) SR, SO2R, wherein R is alkyl, aryl, CF3, F, CH2CF3 or
iii) OR, OTs, OMs, OTf, wherein R is alkyl or aryl.

Unless stated otherwise, for the purpose of the present invention, the term "alkyl group" is intended to mean any linear or branched alkyl group having 1 to 10 carbon atoms, optionally substituted with a functional group, such as, but not limited to, methyl, ethyl or propyl. The term "cycloalkyl" preferably means a cycloalkyl group having 3 to 20 carbon atoms, such as, but not limited to, cyclopropyl, cyclopentyl, cyclohexyl optionally substituted with a functional group. The term "alkyloxy group" is intended to mean any alkoxy group having 1 to 6 linear or branched carbon atoms, optionally substituted with a functional group, such as, but not limited to, OCH3. The term "aryl group" is intended to mean one or more aromatic rings having 5 to 6 carbon atoms, which may be joined or fused, optionally substituted with a functional group, such as, but not limited to, phenyl or pyridyl.

The term "functional group" means halogen atoms, hydroxy, cyano, amino, alkoxy groups as defined above, alkyl groups as defined above or a nitro group.

By "group bearing a pendant basic nitrogen functionality" it is meant herein a group comprising at least one nitrogen atom or amino group, such as represented for example by the structures a to f shown below, wherein the wavy line correspond to the point of attachment to core structure of formula I.

[Chemical structures a, b, c shown]

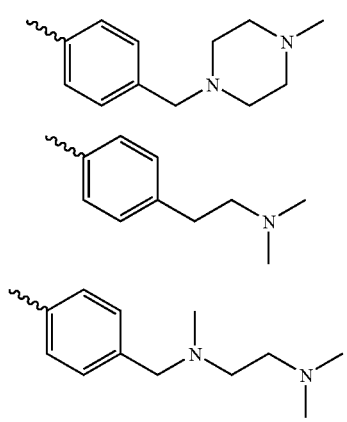

The process of the present invention is carried out in the presence of a suitable base. Suitable bases are organolithium bases (such as but not limited LDA, LiHMDS, n-BuLi, etc.) or metal hydride bases (such as NaH or KH).

The process of the present invention is carried out in a suitable solvent. Suitable solvents are aprotic non-basic solvents such as ethers (such as but not limited tetrahydrofuran, tetrahydropyran, diethyl ether, etc.) or amide (such as but not limited to dimethylformamide, dimethylacetamide, etc.) or halogenated hydrocarbons or mixtures thereof.

The process of the present invention is carried out under a temperature range of −40° C. to 150° C., preferably between −20° C. to 20° C.

The process of the present invention is carried out for a period of time in the range of 5 min. to 24 hours.

The process of the present invention can comprises purification step of the compound of formula (I). Generally, the reaction mixture was poured into water and the precipitate corresponding to the pure compound of formula (I), was collected by filtration. Thus, in one preferred embodiment, the above contemplated process further comprises a work-up using water to precipitate compounds of formula (I).

The invention is illustrated in the experimental details, which follow.

EXAMPLES OF COMPOUNDS SYNTHESIS

The present invention will be illustrated by the following examples, which will not limit the scope of the invention in any way.

General: All chemicals used were commercial reagent grade products. Solvents were of anhydrous commercial grade and were used without further purification. THF was freshly distilled under a stream of argon from sodium and benzophenone. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were realized on a 300 MHz Bruker spectrometer.

Example 1

Preparation of 4-[2-(5-Amino-2-methyl-phenylamino)-oxazol-5-yl]-benzonitrile

Preparation of 4-Oxazol-5-yl-benzonitrile

To a solution of 4-Formyl-benzonitrile (5 g, 38.17 mmol) and tosylmethyl isocyanide (TosMIC) (from Aldrich, 8.33 g, 42 mmol) in MeOH (200 mL) was added K2CO3 (6.85 g, 49.62 mmol) and the mixture was stirred at reflux for 1 h. The solvent was then evaporated and saturated aqueous NaHCO$_3$ was added. The resultant suspension was extracted with dichloromethane (3×100 mL). The combined organic layers were washed with brine (30 mL), dried over anhydrous MgSO$_4$ and concentrated to leave a yellow solid. Trituration with heptane afforded a solid that was collected by filtration and dried under vacuum to give the title compound (6.3 g, 97%). m.p.=140° C.

$^1$H NMR (DMSO-d$^6$) δ=7.91-7.98 (5H, m), 8.58 (1H, s).

Preparation of 4-(2-Chloro-oxazol-5-yl)-benzonitrile

To a solution of 4-Oxazol-5-yl-benzonitrile (3 g, 17.65 mmol) in anhydrous THF (80 mL) at −78° C. under an argon atmosphere was slowly added a solution of LiHMDS (21.2 mL, 1 M in THF, 21.2 mmol). After 1 h at −78° C., solid hexachloroethane (6.275 g, 26.48 mmol) was added. The mixture was then stirred at −78° C. for 1 h and allowed to slowly warm to room temperature and stir for 3 h. The reaction was diluted with AcOEt/H2O (50 mL/15 mL). The organic layer was washed with brine, dried with MgSO4 and filtered. After removal of solvent the solid obtained was recrystallize from Hexane to give the title compound as a white solid (2.95 g, 82%). m.p.=144° C.

$^1$H NMR (DMSO-d$^6$) δ=7.89 (d, J=8.4, 2H); 7.97 (d, J=8.4, 2H); 8.04 (s, 1H).

Preparation of 4-[2-(5-Amino-2-methyl-phenylamino)-oxazol-5-yl]-benzo-nitrile

A solution of N-(5-Amino-2-methyl-phenyl)-acetamide (1.1 g, 6.7 mmol) in DMF (20 mL) was added to a suspension of NaH (402 mg, 10.05 mmol, 60% dispersion in mineral oil) in DMF (20 mL) at 0° C. under an atmosphere of argon. The mixture was stirred for 30 min. at room temperature and cooled to 0° C. A solution of 4-(2-Chloro-oxazol-5-yl)-benzonitrile (1.37 g, 6.7 mmol) in DMF (20 mL) was added dropwise to the mixture. After 30 min., at 0° C., the reaction was poured into ice water (200 mL). The solid was collected by filtration, washed with water, and dried under vacuum to afford the title compound (1.45 g, 75%). m.p.=228° C.

$^1$H NMR (DMSO-d$^6$) δ=2.14 (s, 3H); 4.91 (br s, 2H); 6.25 (dd, J=7.8-1.9, 1H); 6.82 (d, J=8.0, 1H); 7.01 (d, J=2.4, 1H); 7.68 (m, 3H); 7.84 (d, J=8.5, 2H); 9.22 (s, 1H).

Example 2

Preparation of 4-[2-(2-Methyl-5-nitro-phenylamino)-oxazol-5-yl]-benzonitrile

The same procedure outlined above in the preparation of 4-[2-(5-Amino-2-methyl-phenylamino)-oxazol-5-yl]-benzonitrile was used. However N-(2-methyl-5-nitro-phenyl)-acetamide was used instead N-(5-Amino-2-methyl-phenyl)-acetamide. Yield=83%. m.p.>228° C.

$^1$H NMR (DMSO-d$^6$) δ=2.45 (s, 3H); 7.50 (d, J=8.4, 1H); 7.77 (d, J=8.4, 2H); 7.85 (m, 2H); 7.94 (d, J=8.4, 2H); 9.05 (d, J=2.1, 1H); 9.97 (s, 1H).

Example 3

Preparation of 4-[2-(6-Chloro-2-methyl-phenylamino)-oxazol-5-yl]-benzonitrile

The same procedure outlined above in the preparation 4-[2-(5-Amino-2-methyl-phenylamino)-oxazol-5-yl]-benzonitrile was used. However N-(6-chloro-2-methyl-phenyl)-acetamide was used instead N-(5-amino-2-methyl-phenyl)-acetamide. Yield=89%.

$^1$H NMR (DMSO-d$^6$) δ=2.17 (s, 3H); 7.25 (m, 2H); 7.41 (d, J=7.6, 1H); 7.61 (m, 3H); 7.82 (d, J=8.3, 2H); 9.70 (s, 1H).

Example 4

Preparation of 4-[2-(3,5-Dimethoxy-phenylamino)-oxazol-5-yl]-benzonitrile

The same procedure outlined above in the preparation of 4-[2-(5-Amino-2-methyl-phenylamino)-oxazol-5-yl]-benzonitrile was used. However N-(3,5-dimethoxyphenyl)-acetamide was used instead N-(5-amino-2-methyl-phenyl)-acetamide. Yield=85%.

$^1$H NMR (CDCl$_3$) δ=3.80 (s, 6H); 6.20 (s, 1H); 6.70 (s, 2H); 7.30 (s, 1H); 7.57 (d, J=8.0, 2H); 7.64 (d, J=8.0, 2H).

Example 5

Preparation of 4-[2-(2,3-Dimethyl-phenylamino)-oxazol-5-yl]-benzonitrile

The same procedure outlined above in the preparation of 4-[2-(5-Amino-2-methyl-phenylamino)-oxazol-5-yl]-benzonitrile was used. However N-(2,3-dimethylphenyl)-acetamide was used instead N-(5-amino-2-methyl-phenyl)-acetamide. Yield=91%.

$^1$H NMR (CDCl$_3$) δ=2.23 (s, 3H); 2.33 (s, 3H), 6.92 (d, J=7.5, 1H); 7.16 (t, J=7.5, 1H); 7.28 (s, 1H); 7.55 (d, J=8.4, 2H); 7.67 (m, 3H).

Example 6

Preparation of 2-(5-Amino-2-methyl-phenylamino)-oxazole-5-carboxylic acid methyl ester To a solution of glyoxylic acid ethyl ester (50% w/w in toluene) (4 mL, 2 mmol) and Tosmic (3.86 g, 2 mmol) in MeOH (60 mL) was added K2CO3 (5.6 g, 4 mmol) and the mixture was stirred at reflux for 7 h. The solvent was then evaporated and 100 mL of water was added. This solution was saturated with sodium chloride and extracted with diethyl ether. The organic layer was washed with brine, dried (MgSO4) filtered and concentrated to give 1.58 g (60%) of oxazole-5-carboxylic acid methyl ester as white solid. m.p.=35-50° C.

To a solution of oxazole-5-carboxylic acid methyl ester (1.4 g, 11 mmol) in anhydrous THF (50 mL) at −40° C. under an argon atmosphere was slowly added a solution of LiHMDS (13.3 mL, 1 M in THF). After 1 h at −40° C., solid hexachloroethane (3.91 g, 16.5 mmol) was added. The mixture was then allowed to slowly warm to room temperature and stir for 16 h. The reaction was diluted with AcOEt/H2O (30 mL/10 mL). The organic layer was washed with brine, dried with MgSO4 and filtered. After removal of solvent the residue was silica gel column chromatographed (CH2Cl2/Cyclohexane: 1/1) to give 1.1 g of 2-chloro-oxazole-5-carboxylic acid methyl ester (62%) as a white solid. m.p.=35-50° C.

A solution of N-(5-Amino-2-methyl-phenyl)-acetamide (0.51 g, 3.1 mmol) in THF (12 mL) was added to a suspension of NaH (186 mg, 4.65 mmol, 60% dispersion in mineral oil) in THF (12 mL) at 0° C. under an atmosphere of argon. The mixture was stirred for 30 min. at room temperature and cooled to 0° C. A solution of 2-chloro-oxazole-5-carboxylic acid methyl ester (0.5 g, 3.1 mmol) in THF (12 mL) was added dropwise to the mixture. After 30 min., at 0° C., the reaction was poured into ice water (30 mL) and extracted with ethyl acetate. The organic layer was washed with brine, dried (MgSO4) and filtered. After removal of solvent the residue was silica gel column chromatographed (CH2Cl2/Ethanol: 99/1) to give 0.54 g of 2-(5-Amino-2-methyl-phenylamino)-oxazole-5-carboxylic acid methyl ester (71%) as a Colorless syrup.

$^1$H NMR (CDCl$_3$) δ=2.10 (s, 3H); 3.64 (br s, 2H), 3.82 (s, 3H), 6.30 (dd, J=8.0-2.3, 1H); 6.82 (br s, 1H); 6.87 (d, J=8.0, 1H); 7.39 (d, J=2.4, 1H); 7.55 (s, 1H).

Example 7

Preparation of 5-(2-chloropyridin-4-yl)-N-(5-(ethoxymethyl)-2-methylphenyl) oxazol-2-amine A solution of N-(5-(ethoxymethyl)-2-methylphenyl)ethanamide (344 mg, 1.66 mmol) in DMF (5 mL) was added to a suspension of NaH (133 mg, 3.32 mmol, 60% dispersion in mineral oil) in DMF (5 mL) at 0° C. under an atmosphere of argon. The mixture was stirred for 1 h at room temperature and cooled to 0° C. A solution of 2-chloro-5-(2-chloropyridin-4-yl)oxazole (357 mg, 1.66 mmol) in DMF (5 mL) was added dropwise to the mixture. After 1 h at 0° C., the reaction was poured into ice water (20 mL) and extracted with ethyl acetate. The organic layer was washed with brine, dried (MgSO4) and filtered. After removal of solvent the residue was silica gel column chromatographed (CH$_2$Cl$_2$/Ethanol: 98/2) to give 474 mg of 5-(2-chloropyridin-4-yl)-N-(5-(ethoxymethyl)-2-methylphenyl) oxazol-2-amine (83%) as a beige solide.

$^1$H NMR (DMSO-d$^6$) δ=1.15 (t, J=7.0, 3H); 2.27 (s, 3H); 1.48 (q, J=7.0, 2H); 4.42 (s, 2H); 6.99 (d, J=7.6, 1H); 7.19 (d, J=7.7, 1H); 7.46 (d, J=5.3, 1H); 7.58 (s, 1H); 7.73 (s, 1H); 7.89 (s, 1H); 7.37 (d, J=5.3, 1H); 9.64 (s, 1H).

Example 8

Preparation of 5-(3,5-dichloropyridin-4-yl)-N-(5-(ethoxymethyl)-2-methylphenyl) oxazol-2-amine The same procedure outlined above in the preparation of 5-(2-chloropyridin-4-yl)-N-(5-(ethoxymethyl)-2-methylphenyl) oxazol-2-amine was used. However 2-chloro-5-(3,5-dichloropyridin-4-yl)oxazole was used instead 2-chloro-5-(2-chloropyridin-4-yl)oxazole. Yield=81%.

$^1$H NMR (DMSO-d$^6$) δ=1.14 (t, J=7.0, 3H); 2.27 (s, 3H); 1.47 (q, J=7.0, 2H); 4.41 (s, 2H); 6.99 (d, J=7.7, 1H); 7.19 (d, J=7.6, 1H); 7.64 (s, 1H); 7.66 (s, 1H); 8.70 (s, 2H); 9.68 (s, 1H).

Example 9

Preparation of 4-(2-(5-amino-2-methylphenylamino)-4-chlorooxazol-5-yl)-2,6-dimethylbenzonitrile The same procedure outlined above in the preparation of 4-[2-(5-Amino-2-methyl-phenylamino)-oxazol-5-yl]-benzonitrile was used. However 4-(2,4-dichlorooxazol-5-yl)-2,6-dimethylbenzonitrile was used instead 4-(2-Chloro-oxazol-5-yl)-benzonitrile. Yield=74%.

$^1$H NMR (DMSO-d$^6$) δ=2.10 (s, 3H); 2.50 (s, 6H), 5.08 (br s, 2H); 6.32 (dd, J=7.9-1.7, 1H); 6.87 (d, J=8.0, 1H); 6.88 (s, 1H); 7.51 (s, 2H); 9.58 (s, 1H).

The invention claimed is:

1. A process for the preparation of compounds of formula (I), comprising a condensation of a compound of formula (II) and an amide derivative of formula (III), in a solvent comprising a base:

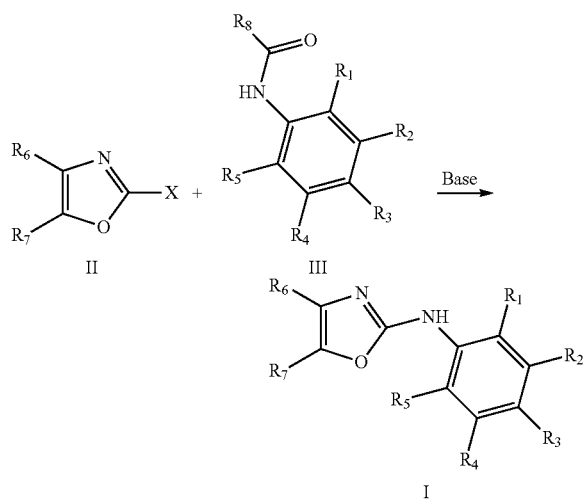

wherein
R1, R2, R3, R4 and R5 each independently are selected from hydrogen, halogen selected from F, Cl, Br or I, a linear or branched alkyl group containing from 1 to 10 carbon atoms and optionally substituted with one or more heteroatoms selected from F, Cl, Br, I, oxygen, and nitrogen, the latter optionally in the form of a pendant basic nitrogen functionality; as well as trifluoromethyl, $C_{1-6}$alkyloxy, amino, $C_{1-6}$alkylamino, di($C_{1-6}$alkyl) amino, carboxyl, cyano, nitro, formyl, hydroxy, and CO—R, COO—R, SO2-R, and SO2NH—R wherein R is a linear or branched alkyl group containing from 1 to 10 carbon atoms and optionally substituted with at least one heteroatom, selected from F, Cl, Br, I, oxygen, and nitrogen, the latter optionally in the form of a pendant basic nitrogen functionality;

R6 and R7 each independently are selected from:
i) hydrogen, F, Cl, Br, I,
ii) an alkyl[1] group defined as a linear, branched or cycloalkyl group containing from 1 to 10 carbon atoms and optionally substituted with one or more heteroatoms selected from F, Cl, Br, I, oxygen, and nitrogen, the latter optionally in the form of a pendant basic nitrogen functionality; as well as trifluoromethyl, carboxyl, cyano, nitro, formyl; as well as CO—R, COO—R, $SO_2$—R, and $SO_2NH$—R wherein R is a linear or branched alkyl group containing from 1 to 10 carbon atoms and optionally substituted with at least one heteroatom selected from F, Cl, Br, I, oxygen, and nitrogen, the latter optionally in the form of a pendant basic nitrogen functionality; as well as a cycloalkyl or aryl[1] or heteroaryl[1] group optionally substituted by a pendant basic nitrogen functionality,
(iii) an aryl[1] group defined as phenyl or a substituted variant thereof bearing any combination, at any one ring position, of one or more substituents selected from:
I, F, Cl, Br;
an alkyl[1] group;
a cycloalkyl or aryl or group optionally substituted by a pendant basic nitrogen functionality;
trifluoromethyl, O-alkyl[1], carboxyl, cyano, nitro, formyl, hydroxy, NH-alkyl[1], N(alkyl[1])(alkyl[1]), and amino, the latter nitrogen substituents optionally in the form of a basic nitrogen functionality; and
$NHSO_2$—R or $NHSO_2NH$—R or CO—R or COO—R or $SO_2$—R or $SO_2NH$—R wherein R corresponds to hydrogen, alkyl[1], aryl,
(iv) a heteroaryl[1] group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents selected from:
F, Cl, Br, I;
an alkyl[1] group;
a cycloalkyl or aryl group optionally substituted by a pendant basic nitrogen functionality,
trifluoromethyl, O-alkyl[1], carboxyl, cyano, nitro, formyl, hydroxy, NH-alkyl[1], N(alkyl[1])(alkyl[1]), and amino, the latter nitrogen substituents optionally in the form of a basic nitrogen functionality; and
$NHSO_2$—R or $NHSO_2NH$—R or CO—R or COO—R or $SO_2$—R or $SO_2NH$—R wherein R corresponds to hydrogen, alkyl[1],
(v) an O-aryl[1], or NH-aryl[1], or O-heteroaryl[1] or NH-heteroaryl[1] group,
(vi) trifluoromethyl, O-alkyl', carboxyl, cyano, nitro, formyl, hydroxy, NH-alkyl[1], N(alkyl[1])(alkyl[1]), and amino, the latter nitrogen substituents optionally in the form of a basic nitrogen functionality, and
(vi) $NHSO_2$—R or $NHSO_2NH$—R or CO—R or COO—R or $SO_2$—R or $SO_2NH$—R wherein R corresponds to hydrogen, alkyl[1] or aryl;
R8 is an alkyl, a cycloalkyl, an aryl or an alkyloxy group, said group being substituted or not with F, Cl, Br or I;
and wherein substituent X is:
i) F, Cl, Br or I, or
ii) SR, or $SO_2R$, wherein R is alkyl, aryl, $CF_3$, F, or $CH_2CF_3$, or
iii) OR, OTs, OMs, or OTf, wherein R is alkyl or aryl.

2. A process according to claim 1, which is carried out in presence of an organolithium bases or a metal hydride base.

3. A process according to claim 1, which is carried out in an aprotic non-basic solvent.

4. A process according to claim 1, which is carried out under a temperature range of −40° C. to 150° C.

5. A process according to claim 1, further comprising a work-up using water to precipitate compounds of formula (I).

6. A process according to claim 2, wherein the organolithium base is selected from LDA, LiHMDS, and n-BuLi, and the metal hydride base is NaH or KH.

7. A process according to claim 3, wherein the aprotic non-basic solvent is selected from ethers, amides, halogenated hydrocarbons and mixtures thereof.

8. A process according to claim 7, wherein the ethers are selected from tetrahydrofuran, tetrahydropyran, and diethyl ether and the amides are selected from dimethylformamide and dimethylacetamide.

9. A process according to claim 4, which is carried out under a temperature range of −20° C. to 20° C.

* * * * *